US008730041B2

(12) United States Patent
Roberts et al.

(10) Patent No.: US 8,730,041 B2
(45) Date of Patent: May 20, 2014

(54) SECURITY SYSTEM FOR A MEDICAL EMERGENCY CRASH CART

(75) Inventors: Carey A Roberts, Wilkes-Barre, PA (US); John H. Welsch, Roaring Brook Township, PA (US); David A. Reppert, Kingston, PA (US); Jeffrey C. Olson, Dallas, PA (US); David J. Salus, Shavertown, PA (US)

(73) Assignee: Metro Industries, Inc., Reno, NV (US)

( * ) Notice: Subject to any disclaimer, the term of this patent is extended or adjusted under 35 U.S.C. 154(b) by 377 days.

(21) Appl. No.: 13/162,058

(22) Filed: Jun. 16, 2011

(65) Prior Publication Data

US 2012/0013464 A1 Jan. 19, 2012

Related U.S. Application Data

(60) Provisional application No. 61/356,228, filed on Jun. 18, 2010.

(51) Int. Cl.
*G08B 13/00* (2006.01)

(52) U.S. Cl.
USPC ........................ 340/541; 340/540; 340/539.12

(58) Field of Classification Search
USPC .......................................................... 340/541
See application file for complete search history.

(56) References Cited

U.S. PATENT DOCUMENTS

| 4,790,610 | A | | 12/1988 | Welch et al. |
|---|---|---|---|---|
| 5,154,497 | A | | 10/1992 | Smith |
| 5,720,535 | A | | 2/1998 | Mehman |
| 5,905,653 | A | * | 5/1999 | Higham et al. ............... 700/244 |
| 6,788,997 | B1 | | 9/2004 | Frederick |
| 2002/0070847 | A1 | * | 6/2002 | Hamilton et al. ........ 340/309.15 |
| 2002/0165641 | A1 | | 11/2002 | Manalang et al. |
| 2004/0065579 | A1 | * | 4/2004 | Wood ............................ 206/545 |
| 2008/0284297 | A1 | | 11/2008 | Olson et al. |
| 2010/0004780 | A1 | | 1/2010 | Rickelhoff |

FOREIGN PATENT DOCUMENTS

WO 2009/158642 A1 12/2009

\* cited by examiner

*Primary Examiner* — Travis Hunnings
(74) *Attorney, Agent, or Firm* — Fitzpatrick, Cella, Harper & Scinto

(57) ABSTRACT

A utility cart includes a sensor or plurality of sensors to determine the state of a cart and secure cart contents. A sensor may be used to determine whether the contents of the cart have been accessed. When the sensor determines that the cart has been accessed, an alarm sequence that sounds an alarm or activates a visual indicator will be initiated. The alarm sequence may be terminated by a kill switch or by using an input device to deactivate the alarm. After the cart is used, the cart is re-stocked and the alarm controller is re-armed to return the cart's alarm system to an access sensing state.

23 Claims, 12 Drawing Sheets

SECURITY SYSTEM FOR A MEDICAL EMERGENCY CRASH CART

BACKGROUND OF THE INVENTION

1. Field of the Invention

The present invention relates to a security system for a mobile utility cart, and more particularly to such a surveillance security system for a medical emergency utility cart commonly called a "medical emergency crash cart" or simply a "crash cart," for medical emergency use in hospitals and other medical institutions. The security system in accordance with the present invention provides the crash cart with one or more indicators for informing a user that the medical cart has been accessed. The indicators provide an alarm condition including one or more of a visual indication, an audible alarm, and remote digital communication unit. The indicators are preferably activated based on detection results from one or more sensors provided on the cart. A mechanism for selectively terminating the alarm condition may also be included.

2. Description of Related Art

A medical emergency crash cart commonly contains medical equipment, instruments, medications and other supplies that may be required while responding to medical emergencies, particularly for medical procedures practiced in cardiac emergencies. In such instances, of course, it is important that the attending doctors and nurses have prompt access to the cart's contents without delay. In other cases, the carts may provide supplies and/or medications for less critical, but still time sensitive, applications. While we use the term "crash cart" below, it will be appreciated that the invention applies to various cart applications, as well as stationary storage cabinets, and may be equipped for any type of medical emergency.

A crash cart generally includes a plurality of compartments such as drawers, shelves, and/or bins for storing medical equipment and supplies such as syringes and medications. Such carts are routinely returned to a pharmacy for restocking after use, so that a full compliment of supplies is available when an emergency or other prompt medical need arises.

The Joint Commission, formerly known as the Joint Commission on Accreditation of Healthcare Organizations (JCAHO), sets forth requirements regarding healthcare organizations and healthcare facilities. Among the requirements set forth by the Joint Commission is the requirement that emergency medications be readily accessible and be secured. These apparently-contradictory requirements necessitate special consideration in emergency situations. Medications are generally considered secured if a) they are in a locked cart, b) the cart is in a locked room, or c) the cart is under constant surveillance or supervision by authorized personnel. Joint Commission audits are focusing increasing attention on the security requirement.

Healthcare organizations and healthcare facilities are hesitant to lock a cart, or to place a cart in a locked room, as such locks can impede the prompt accessibility of the contents of the cart. Mechanical or electronic locks on crash carts or other storage areas have drawbacks, as keys can be lost, pass-codes can be forgotten, locks can jam, and batteries can be dissipated. In light of these drawbacks, when used with emergency crash carts, locks can result in a serious risk to a patient in an emergency situation.

Various methods for securing carts have been considered in the past. For instance, U.S. Pat. No. 4,790,610 (Welch et al.), hereby incorporated by reference, discloses a mechanism for preventing access to a plurality of compartments simultaneously. International Pub. No. WO 2009/158642, hereby incorporated by reference, describes an improved sealing structure for sealing multiple sections of a medical emergency cart which can either simultaneously unlock and unseal a plurality of storage sections or can unlock and unseal one storage section without unlocking and unsealing other storage sections.

Specifically, that international publication discloses that a plastic lock seal may be used to secure access to compartments of the cart. While breakable plastic seals that indicate whether a cart has been accessed have been provided, such seals have drawbacks. For example, the seals do not provide adequate feedback to those supervising the contents of the cart. In addition, an unauthorized person could break the seal and access the cart without the knowledge of hospital personnel if the cart is not in a secure or supervised area. The present inventors believe there is a need for a more proactive way of alerting hospital staff that a cart is being accessed.

While one remedy is to place a cart under constant surveillance to comply with the security requirement for medications, constant surveillance by security personnel is expensive. For these and other reasons, the crash carts and related mechanisms for securing objects stored in utility carts of the prior art are not entirely satisfactory. A need exists for an improved crash cart and related mechanisms for providing suitable accessibility and enhanced security. The present invention addresses that need and overcomes the drawbacks of existing cart options.

SUMMARY OF THE INVENTION

In order to satisfy the requirements for both accessibility and security, the present invention provides "surveillance" of a cart without inhibiting access or requiring excessive vigilance by busy hospital/medical staff. More specifically, the present invention is directed to a cart which is readily accessible, but provides an alert to hospital staff when it is accessed. That alert may be aural, visual, a wireless communication, or a combination thereof. In some embodiments, the alert, or a portion thereof, can be avoided when accessed by an authorized person. It is preferable, however, that hospital staff still be made aware of the use of the cart.

Generally speaking, the present invention will be referred to as a "cart," which may incorporate an enclosed cabinet for storing items, such as medical supplies used in responding to medical emergencies, and which will satisfy the requirements that stored items be both readily accessibility and secure. Typically, a cart of the present invention is a device with one or more compartments that may be opened and closed to access and secure supplies. However, the present invention may be used in conjunction with a variety of storage apparatuses, including medical storage carts, hand-carried storage containers, and stationary storage cabinets, for example.

In one embodiment, the present invention is directed to a cart which includes a housing having a top surface portion and a plurality of sides. A compartment section is also provided for storing items. The compartment section is associated with and accessible from at least one side of the housing. The compartment section may include one or more compartments, such as bins or drawers, which may be placed in (a) a closed condition for preventing removal of items stored therein, and (b) an open condition for permitting access to items stored therein. The housing may, for example, be built around a frame, may be integrally formed, or may include a number of connectable panels. A side is not limited to a vertically orientated surface and may include, for example, a top side surface.

A movable bar may be provided to secure the compartment section in the closed condition. In a preferred embodiment with multiple compartments in the compartment section, a single movable bar may be actuated to secure a plurality of the compartments in the closed condition.

The cart also includes a sensor for sensing access to the contents of the compartment section. For example, the sensor may sense movement of the movable bar. The sensor may also be positioned to sense movement of a drawer or other compartment in the cart. An alarm indicator is provided for signaling an alarm condition (e.g., unsecured access to the cart). An alarm controller is coupled to the sensor and the alarm indicator. An alert, initiated by the alarm controller in response to an alarm condition, is output by the alarm indicator when a signal from the sensor indicates the cart is being accessed. The alarm controller may also initiate a combination of alerts including, for instance, an audible alarm, a visual indication that the cart is being accessed or has been previously accessed, and a wireless message transmitted from the cart to a remote location.

The cart may also include a movement sensor for sensing the movement of the cart itself. An alarm indicator may also indicate an alarm condition corresponding to such movement. The movement sensor may be coupled to an alarm controller which signals an alarm condition when the cart is being moved. The alarm controller may be configured to signal an alarm condition when the movement has been sensed for a predetermined period of time or with respect to a predetermined amount of movement, so that small or inadvertent movement of the cart does not activate the alarm condition. As such, personnel may be made aware that the cart has been displaced from its storage location. This can be used to alert staff of cart use for security reasons and/or to alert staff of the need to replace or restock the cart after a medical use.

While the alerts, such as a siren or horn, are useful in indicating to hospital staff that a cart is being accessed, they can be distracting when handling a medical emergency. Thus, it is preferable to have a kill switch that shuts off the alert. When the kill switch is pressed, an alarm termination signal is transmitted and an alarm indicator will no longer signal an alarm condition. In a preferred embodiment, a kill switch is located inside the compartment section. The kill switch is, thus, inaccessible and hidden from view (and/or access) when said compartment section is in the closed condition. Alternatively, the kill switch may located underneath a lip on the top surface or on the back of the cart. It is preferable, however, that wherever the kill switch is located, the kill switch is not easily visible on the cart. As such, unauthorized users of the cart who are not aware of the position of the switch are not able to easily locate the switch, and hospital personnel will be alerted to unauthorized access events. Preferably, the kill switch is not visible when viewing the front, top, or sides of the cart. While the kill switching may be an actual switch, the term is intended to encompass buttons, toggles, rockers, or other simple electrical or mechanical triggers for sending a termination signal.

In addition, a keypad, or other input device, may also be provided on the cart. The input device may act as a kill switch, in that it may inhibit an alert. Preferably, the input device may be used prior to opening the cart to prevent the alarm signal from initiating, or after opening the cart to shut off the alarm signal. For example, a user of the cart may enter a code into a keypad prior to opening the cart. Thus, authorized personnel can prevent an alarm condition in advance, while unauthorized users cannot. The kill switch and input device may be used to shut off the entire alarm condition, or a part thereof. For instance, an audible indicator may be used to indicate access to the cart for security reasons, while a visual indicator may be used to indicate access for restocking purposes. When the alarm is prevented from sounding the visual indicator may be maintained to indicate to the user that the carts contents have been accessed.

Other input devices may be used in place of the keypad or along with the keypad as an additional input device. Input devices may be provided for identifying the particular user of a cart. If a particular user is identified, it is useful to register user identification information for later identification of the user accessing the cart. For example, a card reader (bar code, magnetic card, proximity card, or smart card), RFID scanner, or biometric feature recognition device (facial, retinal, fingerprint, or speech recognition), may be used. Such input devices may act as advance kill switches as discussed above. Alternatively, the input devices may be used subsequent to the initiation of an alarm condition to terminate the alarm condition. The cart may also be provided with a plurality of user input devices.

The cart may also include a remote digital communication unit, such as a wireless communication unit, so that the alarm condition may be transmitted to remote locations, including workstations and mobile devices. The remote digital communication unit may also include a wired or other remote digital communication device, which may be connected to a network or computing device at a cart storage location. The communication unit of the cart, however, will be referred to in rest the specification as a wireless communication unit, as it is preferred that the cart provides wireless communication, so that the cart does not have to be physically disconnected before it is moved and used. The remote locations may be close by, such as a nurse's station near a cart storage location or may be distributed throughout a building. Remote locations may also be distributed across a wider area, such as across a campus or to distant location which may supervise the carts through video cameras. For example, the alarm condition may be transmitted to a security guard and/or pharmacy location. Alternatively, the alarm condition may be transmitted to a mobile device or plurality of mobile devices (e.g., pagers, cell phones, etc.). The wireless communication unit may also transmit information about what portion of the cart has been accessed, or what user has accessed the cart.

Thus, the alarm indicator may be an audible indicator, a visual indicator, and/or a wireless transmitter (or transceiver). An audible alarm indicator may be a horn for indicating an alarm condition. A visual indicator may be a LED, a plurality of LEDs, an LCD, or other alphanumeric display. The wireless transmitter may include a computer networking device, a Bluetooth device, a mobile telephony device, or radio frequency communication device. When the kill switch is pressed in an alarm condition, the alert, or portion thereof, may be ended.

In another embodiment, the present invention is directed to a cart with multiple storage spaces. The cart includes a housing having a top surface portion and a plurality of sides. The cart also includes a plurality of compartments for storing items in the housing, which are accessible from at least one side of the housing. The compartments are each capable of being placed in either (a) a closed condition for preventing removal of items stored therein, or (b) an open condition for permitting access to items stored therein. The cart also includes a plurality of sensors, each of which is associated with a different one of the plurality of compartments. The sensors determine whether respective compartments are in a closed condition or an open condition.

The sensors can be located near the opening of each of the plurality of compartments, but are preferably on the inside of the cart housing. Each of the plurality of sensors is preferably hidden from view (and/or access) when the plurality of compartments are in closed conditions. When any one of the sensors determines that a compartment section is being accessed, an alarm condition is initiated. The cart further includes an alarm indicator for signaling an alarm condition and may include an alarm controller coupled to the sensors and the alarm indicator. An alarm condition, which activates the alarm indicator, is initiated when a signal from the sensor indicates access to the cart.

A kill switch may be provided at a location known to hospital staff to quickly terminate the alarm condition when the cart is accessed. Preferably, the kill switch is hidden from view, so as not to be readily accessible by unauthorized users. When a kill switch is pressed, an alarm termination signal may be transmitted and an alarm indicator may no longer indicate an alarm condition. Preferably, the kill switch cannot be actuated when the compartment in which the kill switch is located is in the closed condition. Alternatively, a kill switch, for transmitting an alarm termination signal, may be located in a plurality of compartments. A kill switch may be provided in a top portion of the cart, close to an alarm controller. The alarm condition may be terminated when the alarm controller receives the alarm termination signal from any one of the kill switches. Accordingly, the alarm condition may be terminated quickly and easily.

The alarm indicator may be an audible indicator, a visual indicator, and/or a wireless communication unit. An audible alarm indicator may be a horn. The visual indicator may be a blinking light that alerts staff that the cart has been accessed. In addition, a secondary visual indicator may also be activated and stay activated after termination of the alarm condition, to indicate that the cart has been accessed and, thus, may not be fully stocked. As discussed above, a keypad, card reader, or the like may be used to control the alarm condition.

In yet another embodiment, the present invention is directed to method of securing storing medical supplies in a cart. The method includes providing a cart comprising (1) a housing having a top surface portion and a plurality of sides, (2) a compartment section for storing items in the housing and may be placed in (a) a closed condition for preventing removal of items stored in the compartment section, and (b) an open condition for permitting access to items stored in the compartment section, (3) a sensor for sensing movement from the closed condition to the open condition, (4) an alarm indicator for signaling an alarm condition, (5) a termination mechanism for transmitting an alarm termination signal, and (6) an alarm controller, coupled to the sensor, the termination mechanism, and the alarm indicator. Additional steps include arming the alarm controller after medical supplies have been stocked in the storage compartment of the cart and the cart has been placed in the closed condition, and causing the alarm indicator to signal an alarm condition when the alarm controller determines that the sensor has sensed movement from the closed condition to the open condition.

A more complete appreciation along with an understanding of other objects, features, and aspects of the present invention will become apparent from the following detailed description when considered in conjunction with the accompanying drawings.

DETAILED DESCRIPTION OF THE INVENTION

FIGS. 1A through 1E illustrate various views of external and internal features of one embodiment of a crash cart 100 according to the present invention. More particularly, FIGS. 1A through 1E show the cart 100 with certain external enclosures removed so that internal operating mechanisms can be illustrated. In addition, while the present invention is described in the environment of a cart, structures for mounting the cart for movement on a floor, for example, like wheels or casters have been omitted. The features not shown are well within the skill of the art and are not part of the present invention.

Figure 1A:
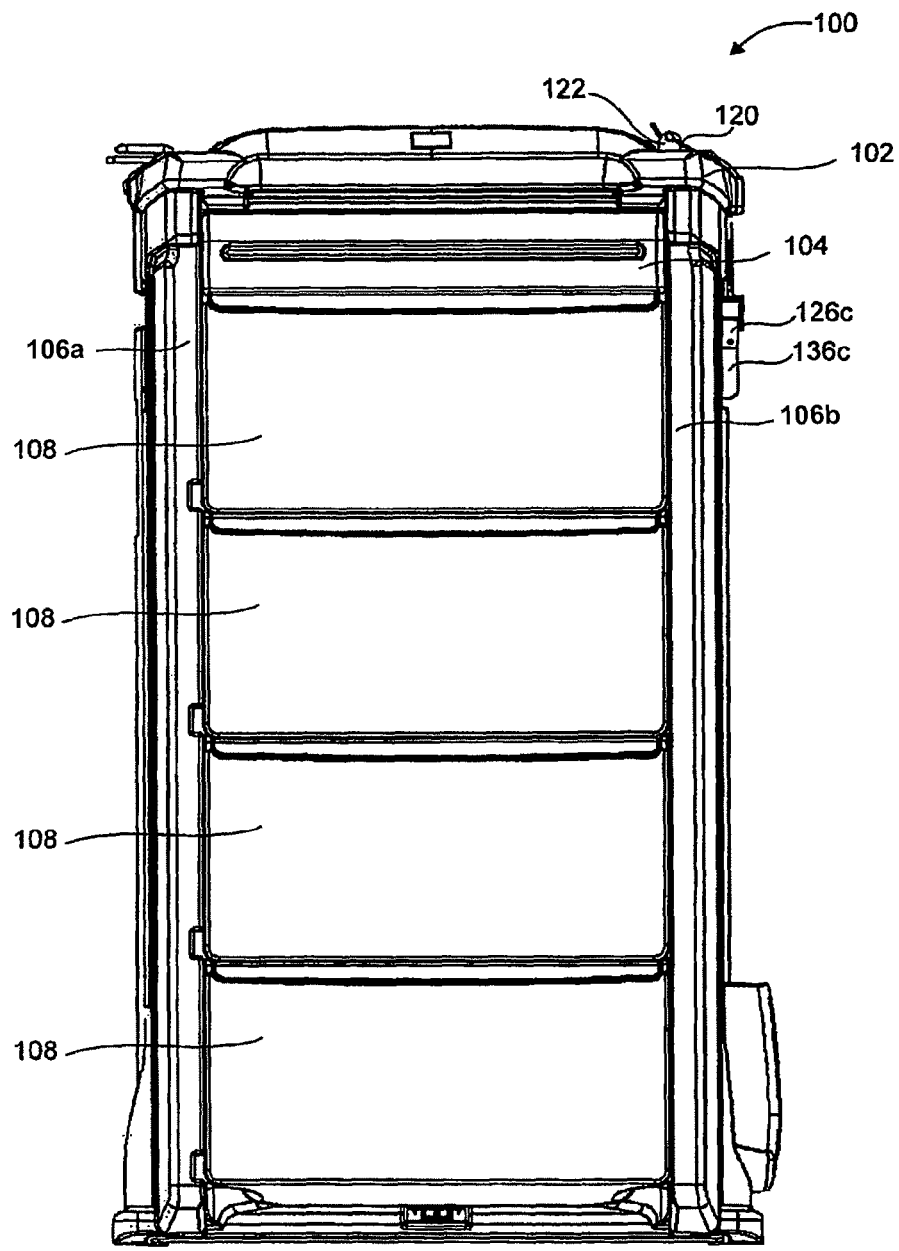
FIG. 1A is a side view of a cart, without wheels, in accordance with the present invention.

FIG. 1A shows one embodiment of a crash cart 100 according to the present invention. As shown in that figure, the crash cart 100 has a substantially rectangular horizontal cross-section or footprint as defined by a top frame 102. The securing bar 122 protrudes through the top frame 102. Four vertical support members are attached to or near respective corners of the top portion 102. These vertical support members provide a compartment which can include multiple tilt-out bins 108 for storing items, such as medical supplies, inside the cart. Side panels (not shown) may be attached to the vertical support members to form an enclosure in which shelves and/or drawers are provided for holding medical supplies. The top frame 102 and vertical support members could be integrally formed, or constructed according to other known techniques without departing from the scope of the invention. For example, the cart may be formed with side panels which provide support for drawers and attach to a top and bottom portion of the cart.

As shown in FIG. 1A, the crash cart 100 in accordance with the invention includes a top frame 102, a side frame 104, a left side frame 106a, and a right side frame 106b. As shown in FIG. 1C, the top frame or component 102, which may be a molded part of the cart 100, may include a tub opening 102a, a securing bar opening 102b, and a sliding top cover retainer bar openings 102c for removably attaching a sliding top cover 110 to the top frame 102 to enclose the tub opening. The left side frame 106a and the right side frame 106b support four substantially identical tilt-out bins 108, in which medical supplies may be stored. A sliding top cover 110 may be removably attached to the top frame 102 to enclose a tub 114 (see FIG. 1F).

The securing bar 122 may either simultaneously allow access to a plurality of storage sections or can allow access to one storage section without accessing other storage sections, as described in WO 2009/158642. One or more sensors are placed in the carts in order to provide the required surveillance of the cart with respect to accessing of the contents of the cart. This can include access to the cart by moving the securing bar 122, opening specific compartments, or a combination thereof (e.g., using securing bars for individual compartments). The sensors are discussed in more detail below.

Figure 1B:
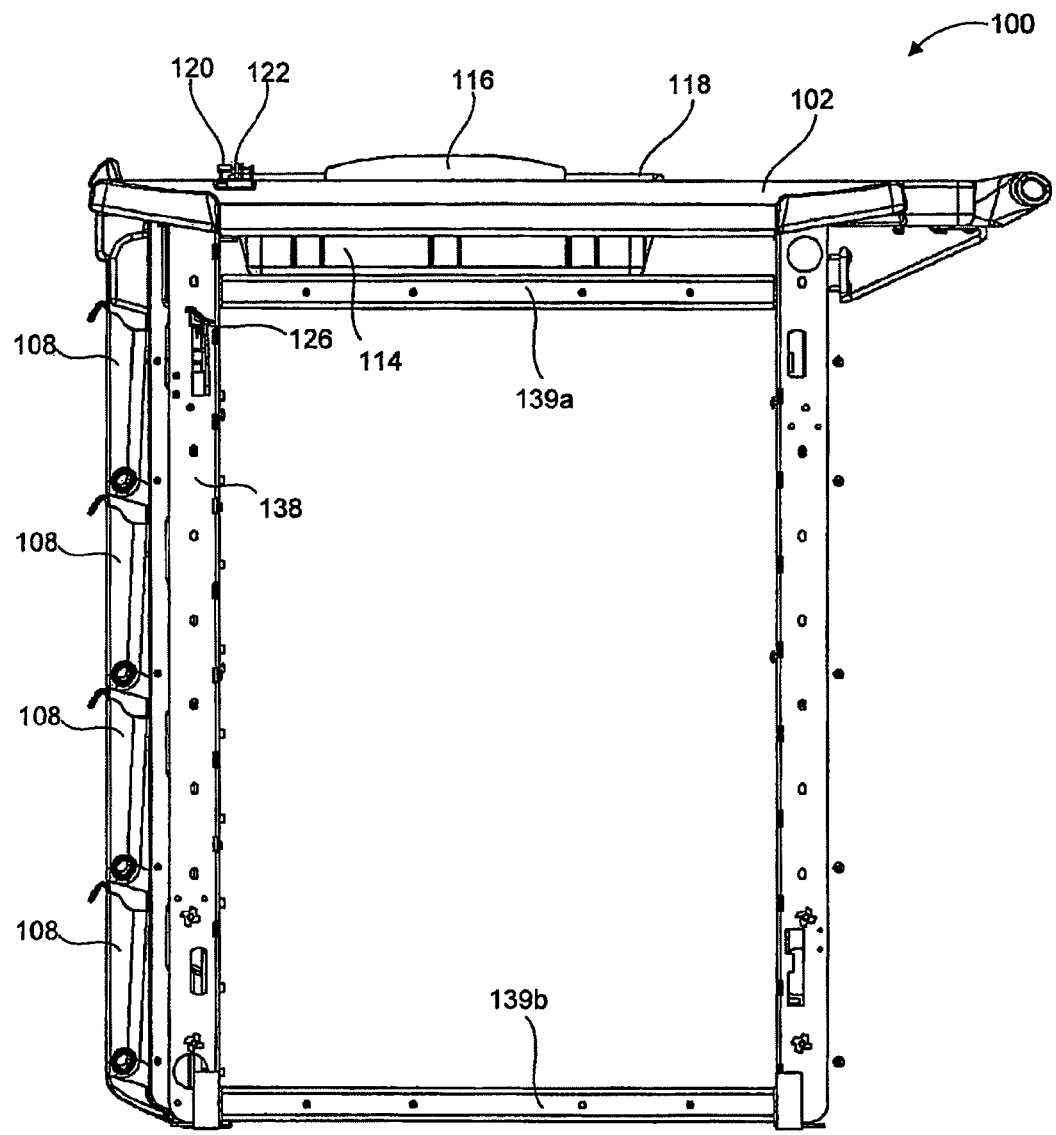
FIG. 1B is a front view of a cart, without drawers or trim panels, in accordance with the present invention.
Figure 1C:
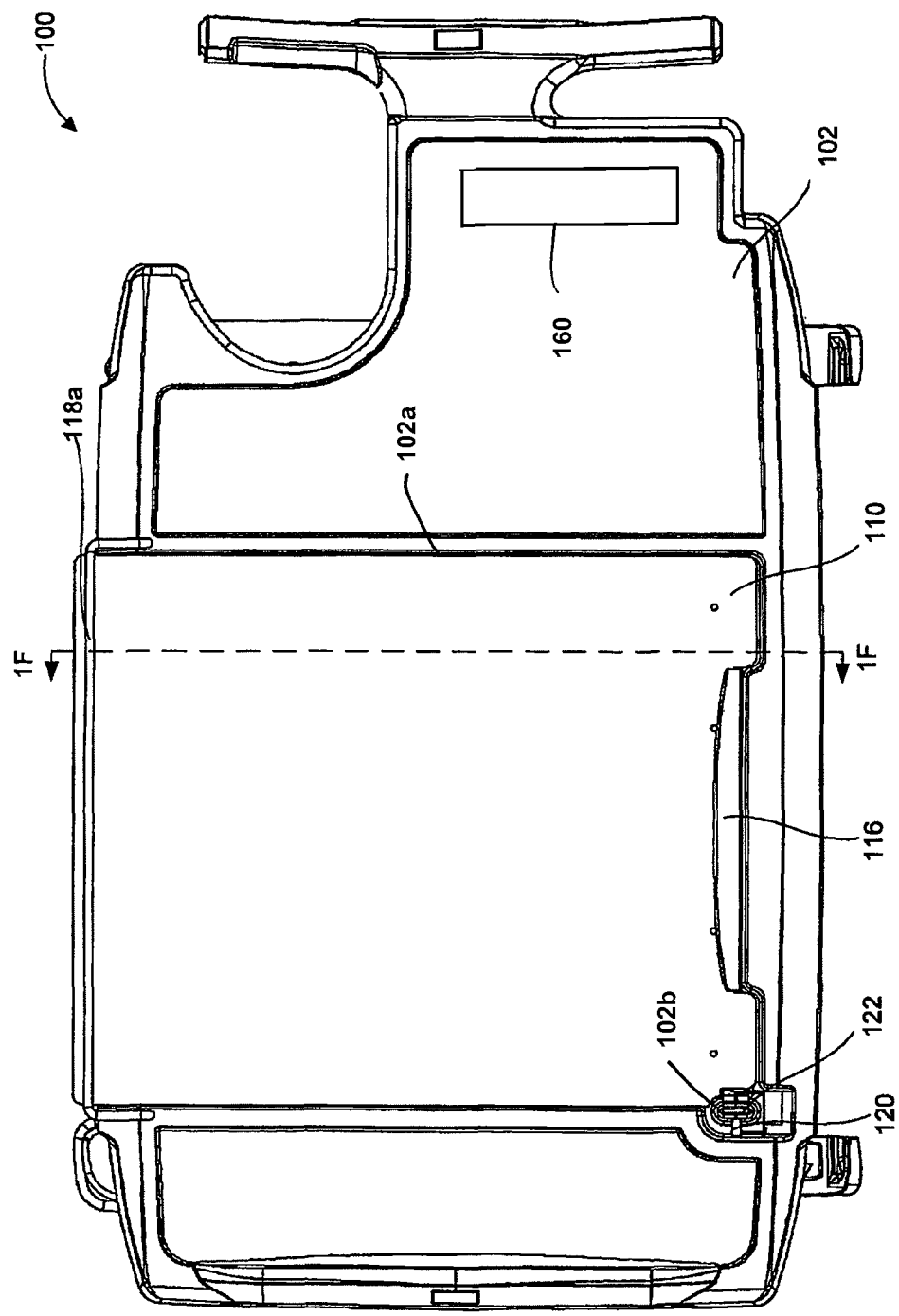
FIG. 1C is a top view of a cart in accordance with the present invention.
Figure 6:
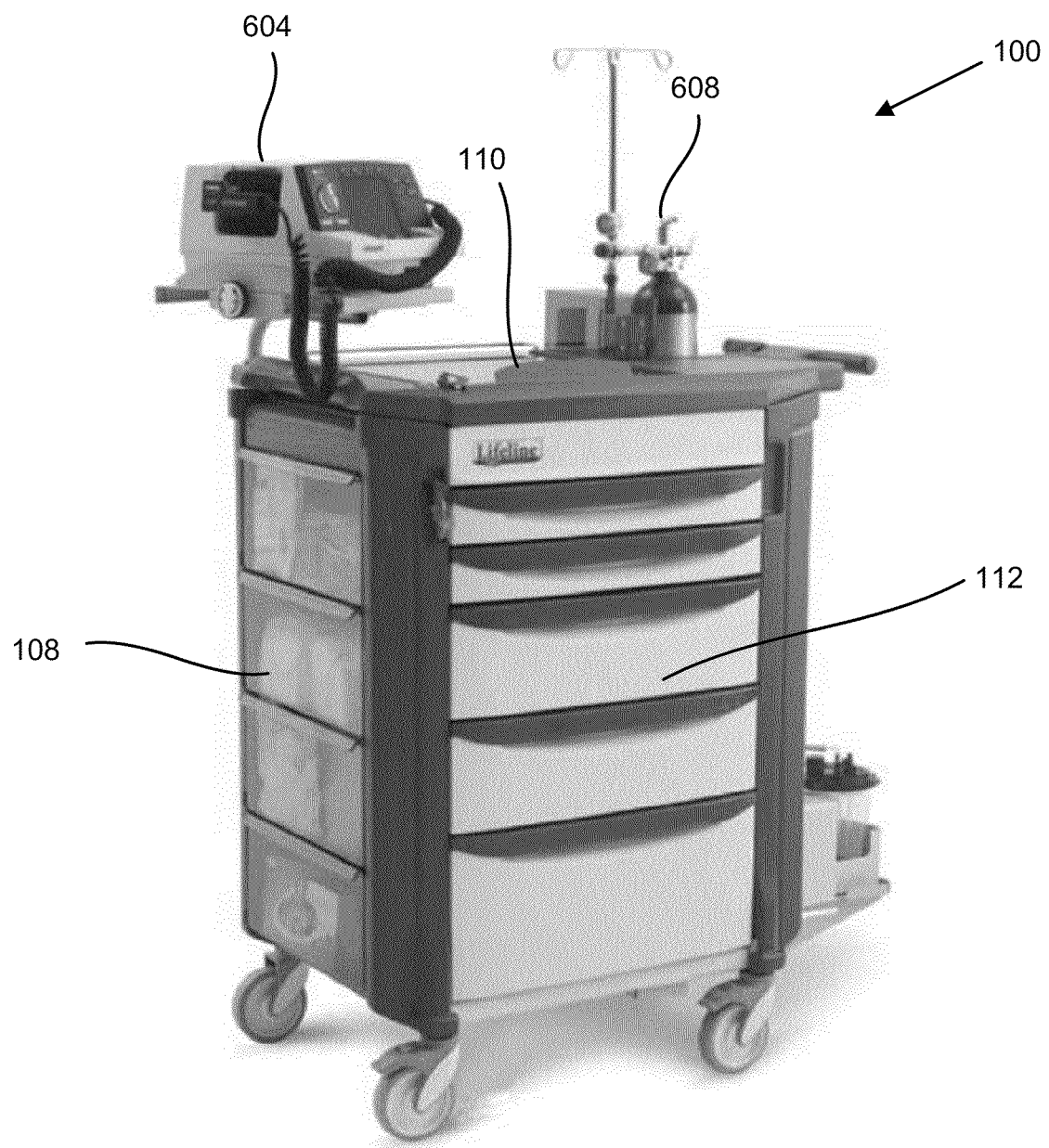
FIG. 6 is a depiction of a partially equipped cart with drawers.

FIG. 1B illustrates a front view of the cart, with portions of the cart removed. In this view, drawers and side panels have been removed to show certain features which may be hidden from view when the cart is completely assembled. The drawers 112, as shown in FIG. 6, would normally be positioned in the body of the cart so that a user standing in front of the cart can access the contents of the carts drawers. As shown in FIG. 1B, a vertical channel 138 is attached to an upper horizontal member 139*a* and a lower horizontal member 139*b* of the cart 100. A manual securing handle 126 may be disposed through the vertical channel 138 and used to prevent the storage sections from opening. A plurality of securing tabs 124*d* of the bin securing bar clips 124 are disposed in front of one of the securing tabs 108*c* of one of the bins 108, which prevents the bins 108 from being opened to secure the bins in a closed condition. To unseal the bins 108, an operator applies a force to the thumb latch 128, which causes the securing handle 126 to pivot away from the securing bar 122 and slide downwardly, which causes the securing bar 122 to move downwardly from a securing position. The securing bar may be moved from the securing position to simultaneously disengage from the securing tab portions to place said plurality compartment sections in the open condition. The securing handle 126 of the securing bar 122 is disposed through an opening in the vertical channel 138. When the securing bar 122 moves downward, the securing tabs 124*d* of the tilt-out bin securing bar clips 124 are lowered from in front of the securing tabs 108*c* of the tilt-out bins 108, which enables the tilt-out bins 108 to be opened by pulling on the bins handles. The securing tabs may also be disposed through openings in the vertical channel 138. Similar elements may be used to secure a plurality of drawers which may be disposed in the cart. It will be appreciated, however, that such seals are not necessary with the alarm system of the present invention. The drawers, as shown in FIG. 6, may be secured in any manner known in the art to prevent them from sliding open when the cart is being moved. It is preferable, however, that the drawers are still easy to open so that the contents of both the drawers and tilt-out bins are easily accessible.

Figure 1D:
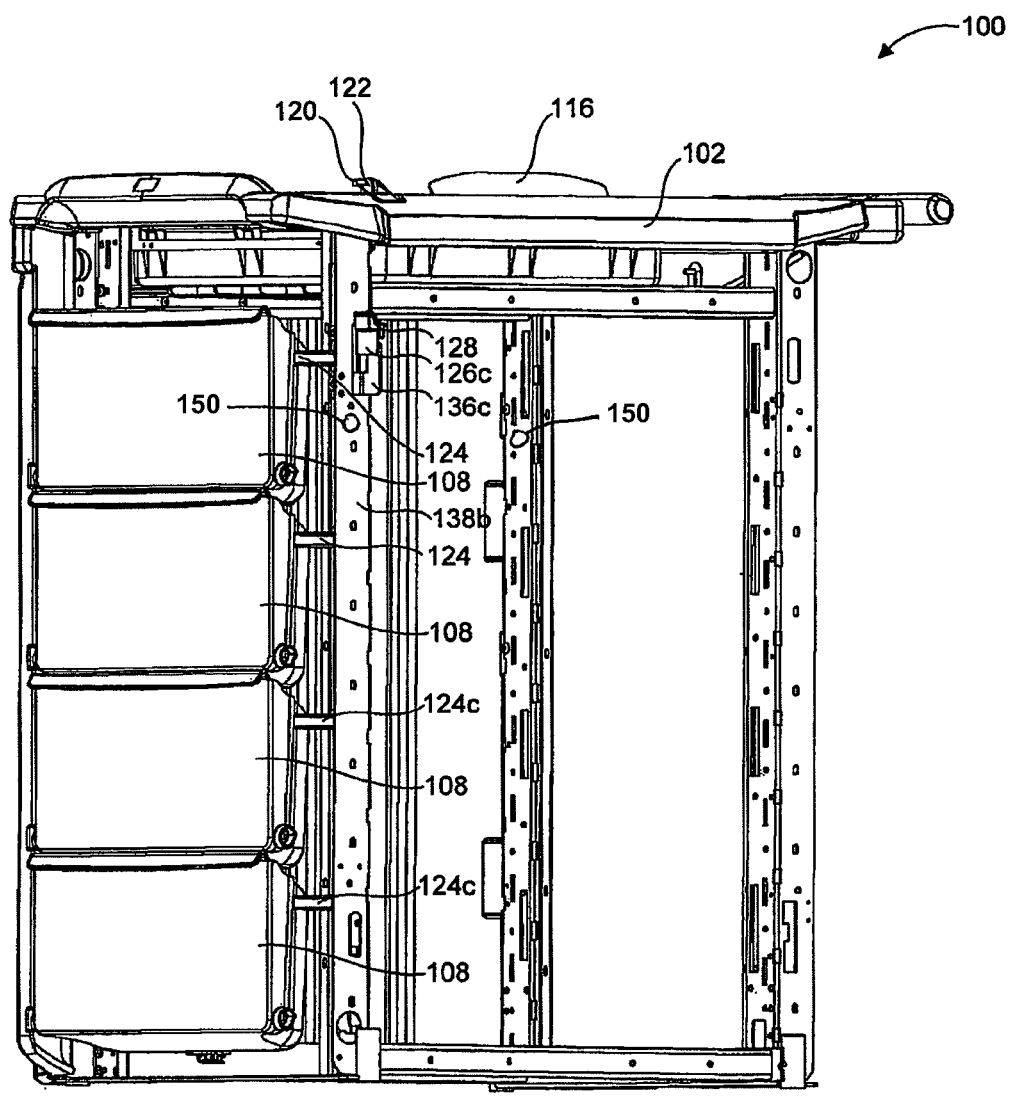
FIG. 1D is a perspective view of a cart, without wheels, panels or drawers, in accordance with the present invention.
Figure 1E:
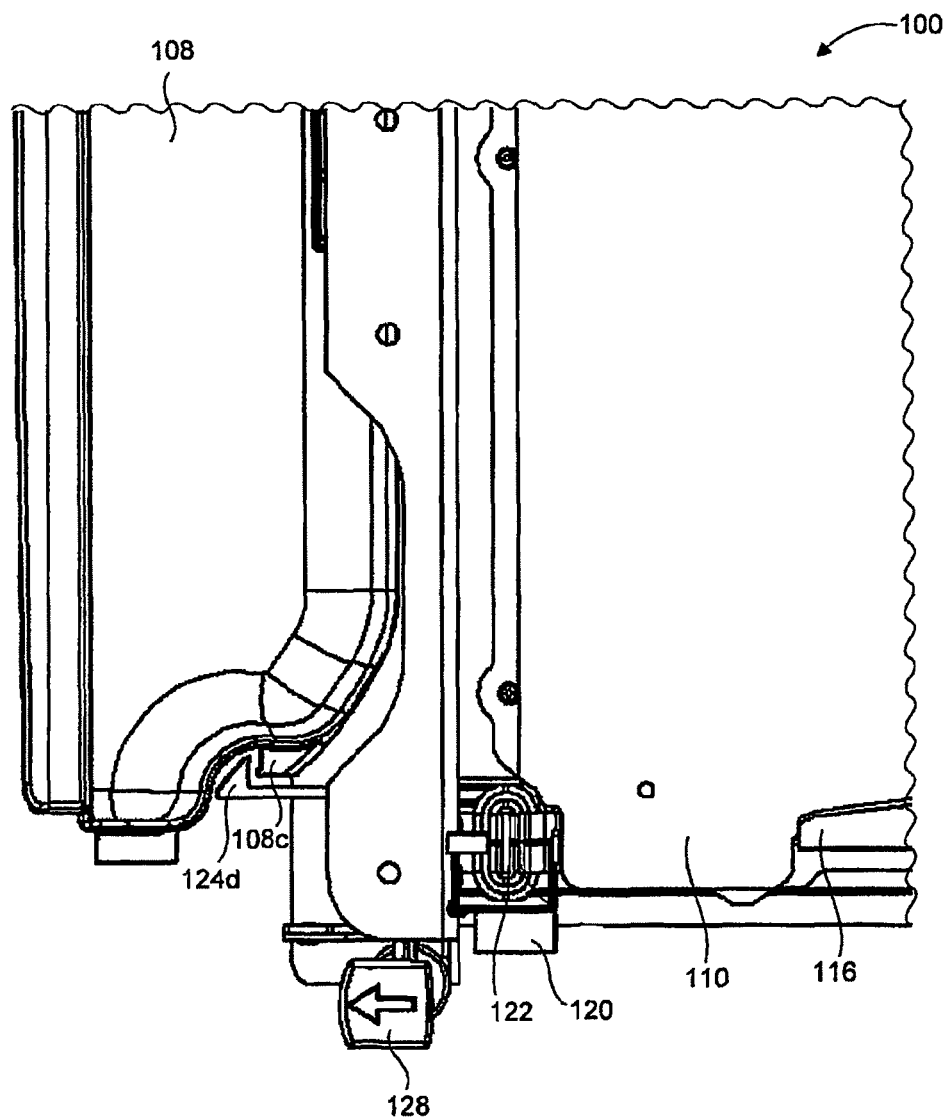
FIG. 1E is an overhead view of the securing bar portion of the cart.

FIG. 1E depicts an overhead view of the securing bar portion of the cart. Each bin 108 includes a securing tab 124*d*, which is part of the bin securing bar clip 124. The securing tab 124*d* is disposed in front of one of the securing tabs 108*c* of one of the bins 108, which prevents the bins 108 from being opened. To release the bins 108, an operator applies a force to the thumb latch 128, which causes the securing handle 126 to pivot away from the securing bar 122 and slide downward, which causes the securing bar 122 to move downwardly. When the movable securing bar 122 moves downward, the securing tabs 124*d* of the tilt-out bin securing bar clips 124 are lowered from in front of the securing tabs 108*c* of the tilt-out bins 108, which enables the tilt-out bins 108 to be opened by pulling on the bin handles, as shown in FIG. 1E. Similar tabs may be provided to engage with a lip or flange of a drawer to allow the drawer to be secured in a closed position.

Figure 2A:
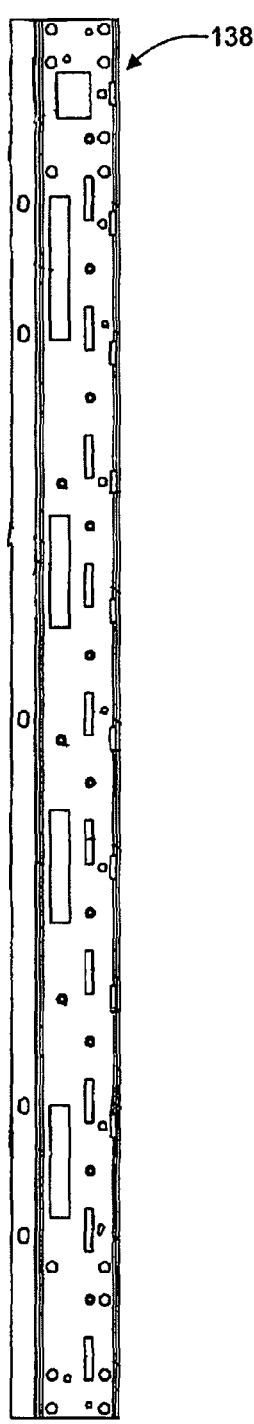
FIGS. 2A and 2B are views of the vertical channel illustrated in FIG. 1.
Figure 2B:
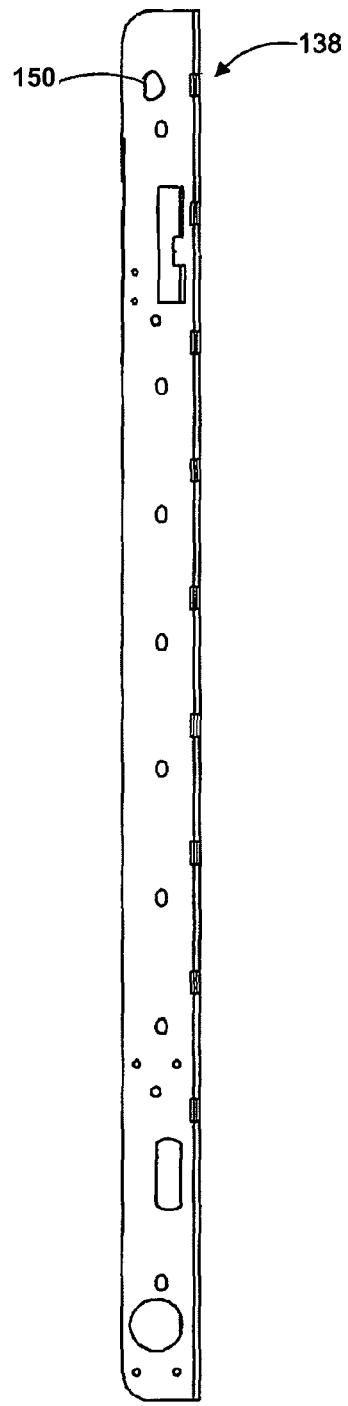

A securing bar sensor 150 may be attached to the vertical channel 138, as shown in FIGS. 2A and 2B, to sense the movement of the securing bar 122 to an open position to unseal the storage compartments. The sensor may be located on an inside portion of the vertical channel which is opposed to the securing bar 122. When the securing bar 122 is moved from the closed position, the sensor sense that the securing bar is moved and that the storage compartments have been placed in the open condition. When a securing bar is not used, a plurality of sensors may be located on an inside portion of one of the rear vertical channels, or directly inside the bins or drawers, to directly sense movement of the bins or drawers from a closed condition to an open condition.

Alternatively, the movable securing bar may be designed to engage with only bins or only drawers, or any combination thereof. As such, the securing bar may secure only particular bins or drawers, so that unsecured bins or drawers remain freely accessible. As such, certain drawers or bins may be accessed independent of the sensor.

The securing bar sensor 150 may be a magnetic sensor or another type of movement or displacement sensor. In order to allow drawers or bins to be opened, the securing bar moves downward. The securing bar sensor senses that movement, and signals the cart to initiate an alarm sequence. The vertical channel is depicted in FIG. 2. The sensor 150 may attached to the vertical channel 138 or the movable securing bar 122, or may be located anywhere along the path of the securing bar 122, as long as the sensor can detect movement of the securing bar. The securing bar may be additionally secured using a bar seal 120, shown in FIG. 1C. Plastic seals are known in the art to indicate access to a cart. However, while such a physical seal indicates access to the contents stored in the cart, it is preferable to provide an indicator that does not require close inspection of the cart to determine if a cart has been or is being accessed. It is contemplated, however, that these options may be used together. While the sensor is shown with respect to the movable bar 122, the sensors may sense movement of the compartments or drawers of the cart. Specifically, sensors may be incorporated directly with the drawers to sense movement thereof.

Figure 5:
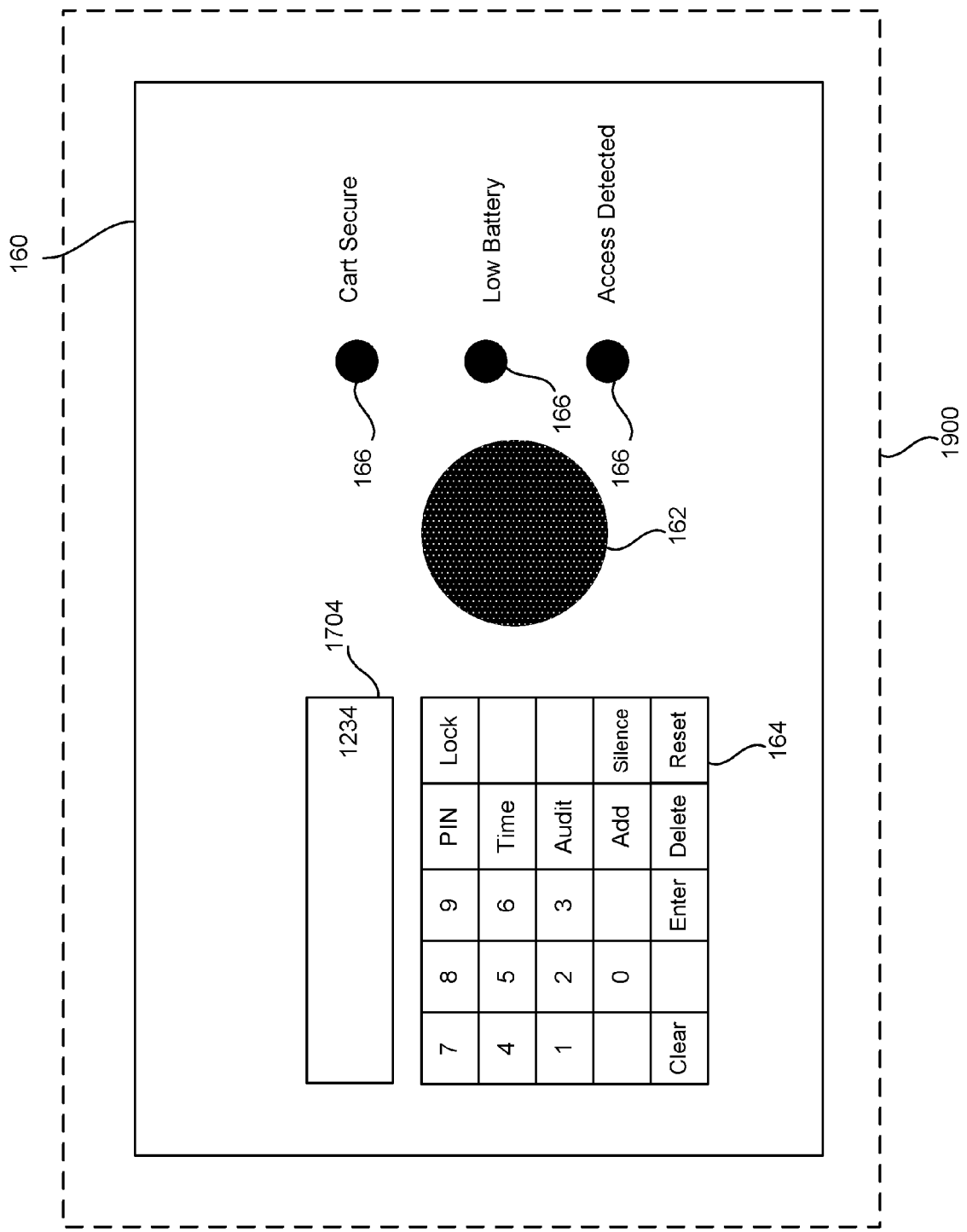
FIG. 5 is a diagram of the cart alarm control system.

FIG. 1C illustrates a top view of an example top frame or component 102 of the cart 100. The top frame 102 may be a molded part which can be attached to side panels or to a frame to which side panels are attached. For example, FIG. 1D is a perspective view of the cart which shows a top frame attached to a plurality of vertical channels. An upper portion of the top frame 102 includes a tub opening 102*a*, a securing bar opening through which the securing bar 122 is disposed, and sliding top cover 110 with a sliding top cover pull plate 116. The upper portion of the top frame may also be the location of the visual indicator, input devices and/or audible indicator. Preferably, these devices are centrally located in a control unit 160. As shown in FIG. 5, the control unit 160 includes an audio output 162, a keypad 164, and a plurality of LEDs 166 for outputting cart information. The control unit may be located elsewhere (and at multiple positions) on the cart, though it is preferable that the control unit is located at or near the top surface of the cart, to allow information to be easily conveyed to and from the user of the cart.

To secure the contents of the carts, the sensor 150 is coupled to an indicator, which may be aural or visual, so that a potential user of a cart or hospital personnel is alerted to the fact that the cart is being accessed. This provides security, as required by the Joint Commission. The indicator may also indicate that the cart has been previously accessed and, thus, may not contain a full complement of supplies. Preferably, the audible indicator 162 is a horn, buzzer, siren or speaker. The audible indicator is preferably activated when the cart is accessed. When the sensor indicates the opening of the cart, the alarm sounds. This provides for surveillance of cart access by hospital personnel without requiring personnel to dedicate themselves to full-time visual monitoring of the cart.

When the alarm is silenced, however, the cart may still need to indicate that it has been accessed and may no longer be fully stocked. As such, the alarm system may also include one or more visual indicators such as an LED 166 or other display device to be used either as an alternative to or in combination with the audible security indicator 162. The visual indicator may include multiple lights or another visual display. For instance, a flashing light may indicate that the cart has been accessed, until the alarm condition is terminated. Another light or display may indicate the status of the cart even after the alarm condition of the security indicator has been terminated. That is, while a termination mechanism such as a kill switch will terminate an audible alarm and/or flashing lights, the cart will still indicate to a potential user that the cart has been accessed. Therefore, a potential user will be made aware that the cart may no longer contain the full complement of supplies. The visual indicator 166 may also be used to present other information, such as the status of the battery which powers the alarm system.

Preferably, a visual indicator includes one or more LEDs. The visual indicator may also be an LCD display. Alternatively, the visual indicator may include both an LCD display and one or more LEDs. The visual indicator is activated when the cart is accessed or when a low battery is detected.

An alarm system controller, coupled to the alarm indicator, may be included in the cart to control the state of the indicator. The alarm controller may be implemented by a processor, CPU, ASIC, PLD/FPGA, or other electronic controller devices. The alarm system may also include an input device for receiving a reset command from a user or from a separate computing device. A reset command may be from the kill switch, which would shut off an indicator indicative of an alarm condition. The reset command may be differentiated from the alarm termination signal by requiring that the switch be activated in a particular sequence or for a particular duration. The reset command may also be initiated by the returning the storage compartments to the closed condition or securing the storage compartments in the closed condition with the movable bar. Alternatively, the reset command may be provided later to reset a visual (or other) indicator indicating that the cart needs to be restocked. The reset command will indicate that the cart has been restocked and return the cart to an access detecting state. Thus, indicators of an alarm condition can be reset with use of a kill switch and the closing of a compartment and/or security bar, while the indicator of stocking needs may be controlled separately. As such, the present invention may effectively seal the cart so that use of carts can be easily determined and the contents of the cart may be restocked as needed.

If an LED is utilized, the LED may be in an off state when the cart is fully stocked and be activated when the cart's contents are accessed. Multiple colors and/or blinking patterns may be presented in one LED element to indicate a variety of different cart conditions, including a secure condition, an alarm condition, a previously accessed condition, and a low battery state. Preferably, the visual indicator is located on the top portion of the cart, so that the indication of access to the cart is readily apparent to a potential user of the cart and to personnel in charge of making sure that carts are fully stocked.

As discussed above, the cart may also include a hidden "kill" switch 180 to deactivate the indicator(s). Kill switch may be used to terminate a portion or all of the alarm condition. In a preferable embodiment, the kill switch terminates only the audio indicator portion of the alarm condition. When the kill switch is used to terminate the entire alarm condition, it is preferable that an additional visual indicator indicate that the cart has been accessed. The kill switch may be located in a drawer of the storage compartment. Alternatively, the kill switch may be located on the exterior of the cart body. Preferably, if the kill switch is located on the exterior of the cart, the switch is hidden from view, below a lip on the top side surface or back of the cart, so that it is not directly visible to the user who does not know the location of the kill switch. That is, when an unauthorized person is looking at the cart, the unauthorized person will not easily notice and identify the kill switch on the cart. Authorized personnel, however, will know the location and will be able to use the kill switch to prevent at least the audio portion of the alarm condition. The indicators may make it difficult to concentrate and communicate when dealing with emergency situations. As such, the kill switch allows a user to turn off the alarm condition after the cart's contents are accessed.

Preferably, when a securing bar is used, one kill switch is used and is accessible only after the securing bar has been moved to set off the alarm condition. The kill switch of the present invention may be provided interior to one of a plurality of compartments, so that the kill switch cannot be activated before or concurrently with the triggering of the alarm condition. In other embodiments, no securing bar is used, or the securing bar does not secure all of the storage compartments. As such, in some cases, a kill switch may be provided inside each of the tilt-out bin or drawer cavities, so that when the bins or drawers are opened, a user who knows of the location of the kill switch will easily be able to terminate the alarm. In other embodiments, a master kill switch for all of the drawers may be provided. Thus, with the kill switch, the alarm can be quickly silenced by someone who knows of the location of the kill switch.

Alternatively, a keypad may be used to allow an authorized person to disable the alarm before (or after) opening the cart. In either case, however, the cart can be opened without delay whether or not the clinician has a code, access card, key, etc.

Specifically, the cart may also include a keypad 164 into which a code would be entered. The keypad may terminate the alarm condition in the same manner as the hidden kill switch. That is, the keypad 164 allows the indicator(s) to be turned off when the cart is accessed. The keypad may also be programmed to allow the indicator(s) to be deactivated before an alarm condition is initiated. Specifically, authorized persons may be given pin codes that can deactivate the alarm indicator(s) before the cart is opened. However, an indicator of the need to restock the cart and a battery status indicator is still preferably provided. The deactivation of the indicator may be limited to access of the cart detected within a predetermined period of time after the entry of the code. As such, the cart may be able to recognize that the cart was not actually accessed after the code was entered or just reset at a predetermined time after entry of the pin. Thus, the cart will remain in a secure state. The system can be reset upon closing of the compartment, entering another code, or use of a reset button. The kill switch 180 may be used in situations where a key code is forgotten or lost. As such, the items stored in the cart remain readily accessible, yet the alarm provides for consistent surveillance.

In yet another embodiment, the cart may include another type of input device, in addition to or as an alternative to a keypad. For example, a card reader 1728, which may be used to read a proximity card (e.g., a RFID card), a magnetic card (including a magnetic stripe card), a smart card, a bar coded card. A biometric feature recognition device, which may recognize at least one of facial, retinal, fingerprint or speech characteristics, may be used. The input devices may receive a logical key, which indicates authorized access to the cart or may contain alarm condition termination information. The logical key may include information such as a key code or password, a card identifier, or a biometric feature of a user. As such, an identification card or personal feature may be used to identify the particular user accessing the cart. The alarm controller may be configured so that the alarm indicator may be turned off by a person authorized to access the cart, but so that the alarm indicator cannot be turned off by an unauthorized person. In a more preferable embodiment, if a particular user is identified, the user identification information is stored in a memory. Other information, regarding the time, access, or type of access (e.g., which compartment) may also be stored.

As discussed, the alarm condition may be provided by a wireless communication. This may be in addition to or instead of audible and/or visual alerts at the cart. In a preferable embodiment, however, the wireless communication unit is used in combination with an alarm indicator present on the cart. The cart may include a wireless communication unit 1730, so that the alarm condition may be transmitted to remote locations, workstations, or devices. The wireless device may be integrated into the alarm controller, or may be a separate device that is coupled to the alarm controller. The wireless communication unit may communicate with other computing devices directly or over a network. For example, the wireless communication unit may communicate over a 802.11n network. The wireless communication unit may be used to transmit cart access information to a remote site, including user identity, time of access, compartments being accessed, etc.

Preferably, the wireless communication device is able to transmit a signal to a nurse's station or other locations, so that desired personnel are alerted that the cart has been accessed. For example, the wireless communication unit may transmit a signal to a computer at the nurse's station that indicates that the cart is being accessed, which may include visual and/or audible alerts at the nurse's station rather than (or in addition to) at the cart. In addition, the communication may be stored to reflect that a cart was accessed at a particular time. As such, the personnel will be alerted that they should not depend on the availability of that cart or that a full complement of supplies may not be available in that cart.

The alarm condition may be transmitted to a supervisory location or to a pharmacy or other restocking location. As such, when the cart has been accessed, a person in the pharmacy may be notified that a replacement cart is necessary and/or that a cart in a particular location may need to be inventoried and restocked. Alternatively, the alarm condition may be transmitted to a mobile device or plurality of mobile devices. For example, a text alert may be transmitted to personnel in charge of replacing or restocking the cart or to personnel assigned to an area where that cart may be used (e.g., nurses, security, etc.).

The wireless communication unit may also transmit information about which user has accessed the cart. An alarm condition may also be transmitted to be monitored by security personnel. If an alarm condition is triggered and a coded alarm termination signal is not received from a cart input device within a predetermined period of time, security personnel may be alerted to the cart access. If an unauthorized person has entered information to deactivate the alarm condition, the security personnel may be notified of the unauthorized access. As such, security personnel may be alerted to the presence of persons who may be stealing items stored in the cart.

The wireless communication unit may also transmit information about what portion of the cart has been accessed. If a plurality of sensors are provided in the cart to monitor access to each of a plurality of storage compartments, the wireless communication unit may be able to transmit information indicating that only one particular drawer has been accessed. For example, the cart's wireless communication unit may be able to transmit information to a pharmacy in charge of restocking the cart indicating that only a top drawer has been accessed. Of course, such information may also be stored in the cart for later retrieval, whether or not wireless communication unit is provided. As such, the pharmacy may be able to restock the cart quickly by bringing supplies necessary to restock the top drawer, without having to retrieve and/or inventory the entire cart. Accordingly, the cart may be restored to a fully stocked condition in a shorter period of time than if the cart was retrieved and returned to the pharmacy for a full inventory and restocking process.

Figure 1F:
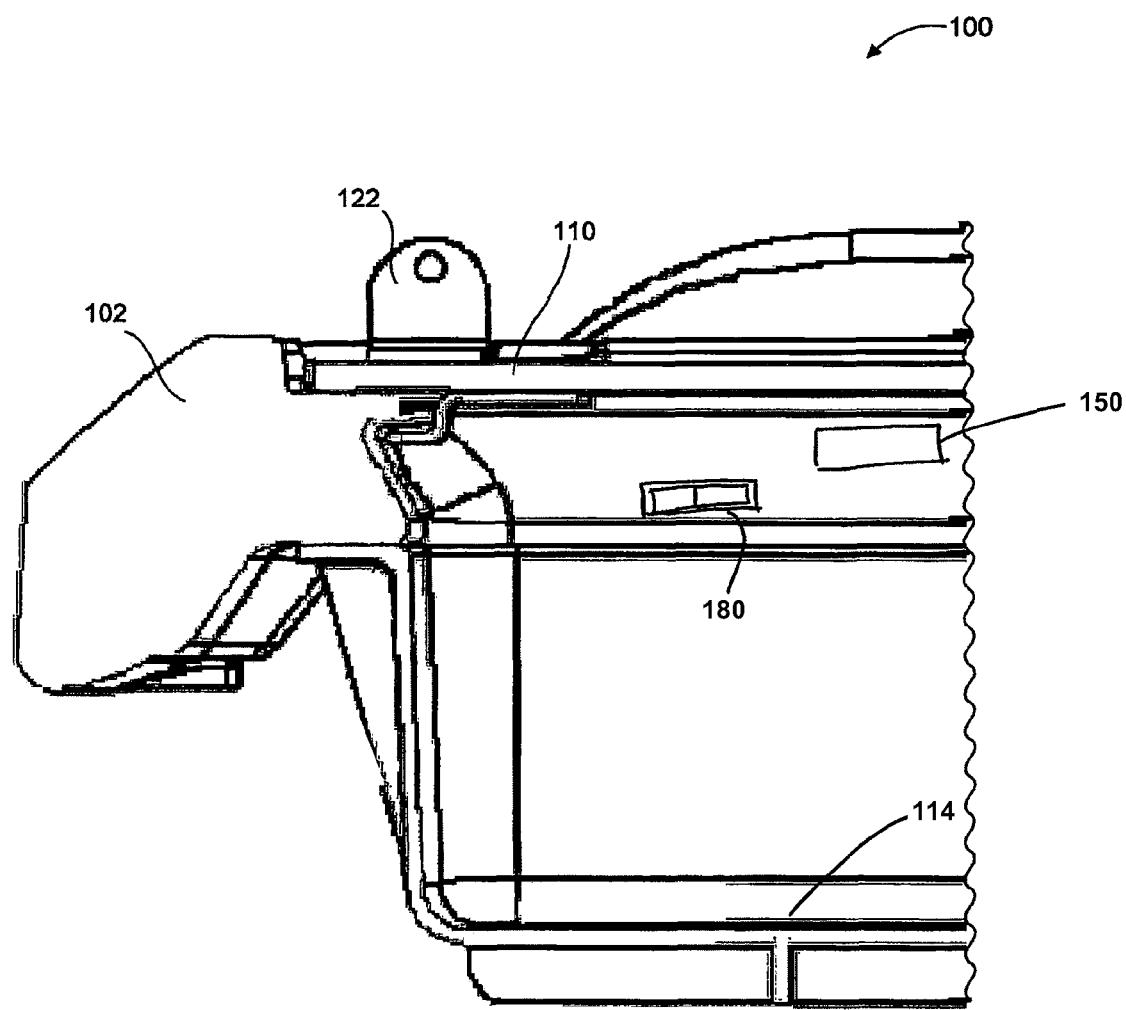
FIG. 1F is a partial cross-sectional view of a top portion of the cart taken along line 1F-1F in FIG. 1C.

FIG. 1F depicts partial cross-sectional view taken along line 1F-1F in FIG. 1C and looking in the direction of the arrows, respectively, of certain external and internal features of a preferred embodiment of a crash cart in accordance with the present invention. A tub 114 may be placed in the tub opening 102a in the top frame 102, or supplies may be placed directly into the top frame 102 below the top cover 110. A sensor 150 may be placed in the top frame 102 to sense movement of the top cover 110. A kill switch 180 may also be placed beneath the top cover 110 in order to terminate an alarm that is activated by movement sensed by the sensor.

Figure 3A:
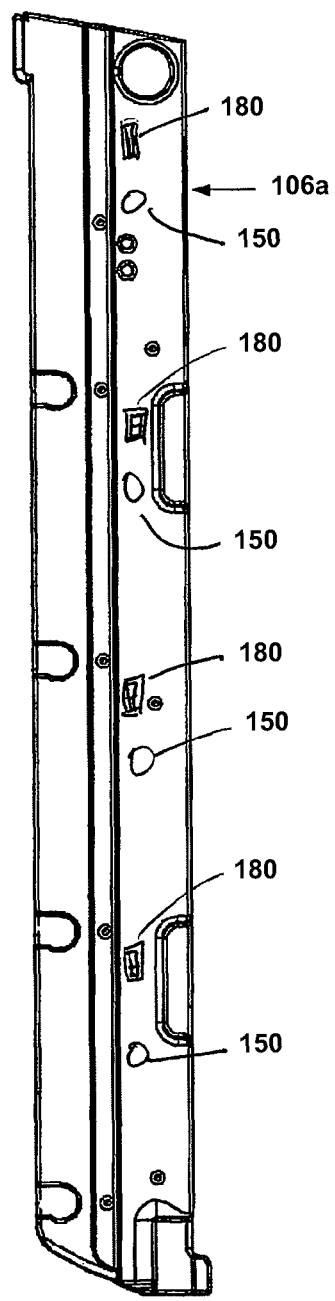
FIGS. 3A and 3B are views of a left side trim panel and a right side trim panel, respectively.
Figure 3B:
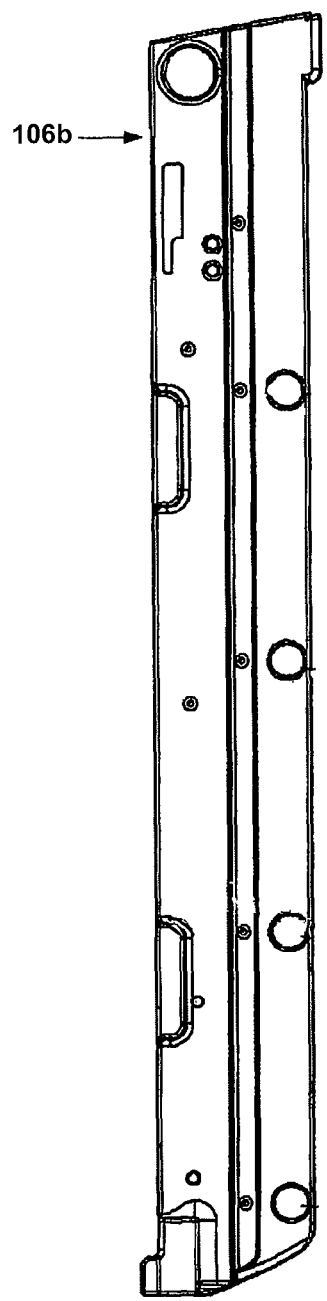

To achieve preferred embodiments discussed above, multiple sensors may be attached to individual compartments or drawers. FIGS. 3A and 3B depict a right side view of the left side frame 106a and a left side view of the right side frame 106b. Tilt-out bins 108 mounted into the side of the cart 100, will be received by the recesses of the left and right side frames. A plurality of sensors 150 and kill switches 180 may be provided near the recesses of the left side frame 106a in order to determine attempts to access the contents of the cart stored in the tilt-out bins 108. As such, the present invention may be applied to carts that do not include a securing bar for accessing multiple compartments. Multiple sensors 150 may be tied to multiple aural or visual indicators so that access to each of the drawers may be sensed individually. A plurality of LEDs may be located on the control unit 160 of the top frame 102 or distributed along the left or right side frame. Alternatively, a common display element may be provided in order to provide drawer specific information without the need for multiple LEDs.

When multiple sensors are employed, an alarm condition triggered by any one of the sensors may be terminated by a kill switch. The kill switch may be located near the top of the cart so that it is easy to find and access. Preferably, a kill switch may be provided inside a top compartment, so that anyone who knows the location of the kill switch may quickly and easily terminate an alarm condition. Alternatively, multiple kill switches 180 may also be placed inside the cart near a drawer member 112 or near a bin 108, in order to terminate an alarm that is activated by movement sensed by individual drawer or bin access sensors.

The alarm may be reactivated once the compartment or security bar is placed in the closed condition. For instance, the movable securing bar may be raised to the latched position to re-arm the cart's alarm system. Alternatively, cart's alarm system may be activated or deactivated and re-armed by another input element, including a switch, a keypad button, a card reader, or other control mechanisms discussed herein. When a securing bar is not used, or when each compartment and sensor provides the function of the securing bar, a keypad may be used to enter information and reset the cart's alarm system. Alternatively, an I/O port, or wireless communication unit, may be provided to rearm the cart's alarm system using a computer or handheld computing device. In yet other embodiments, the closing of the drawer itself will rearm the system.

Figure 4:
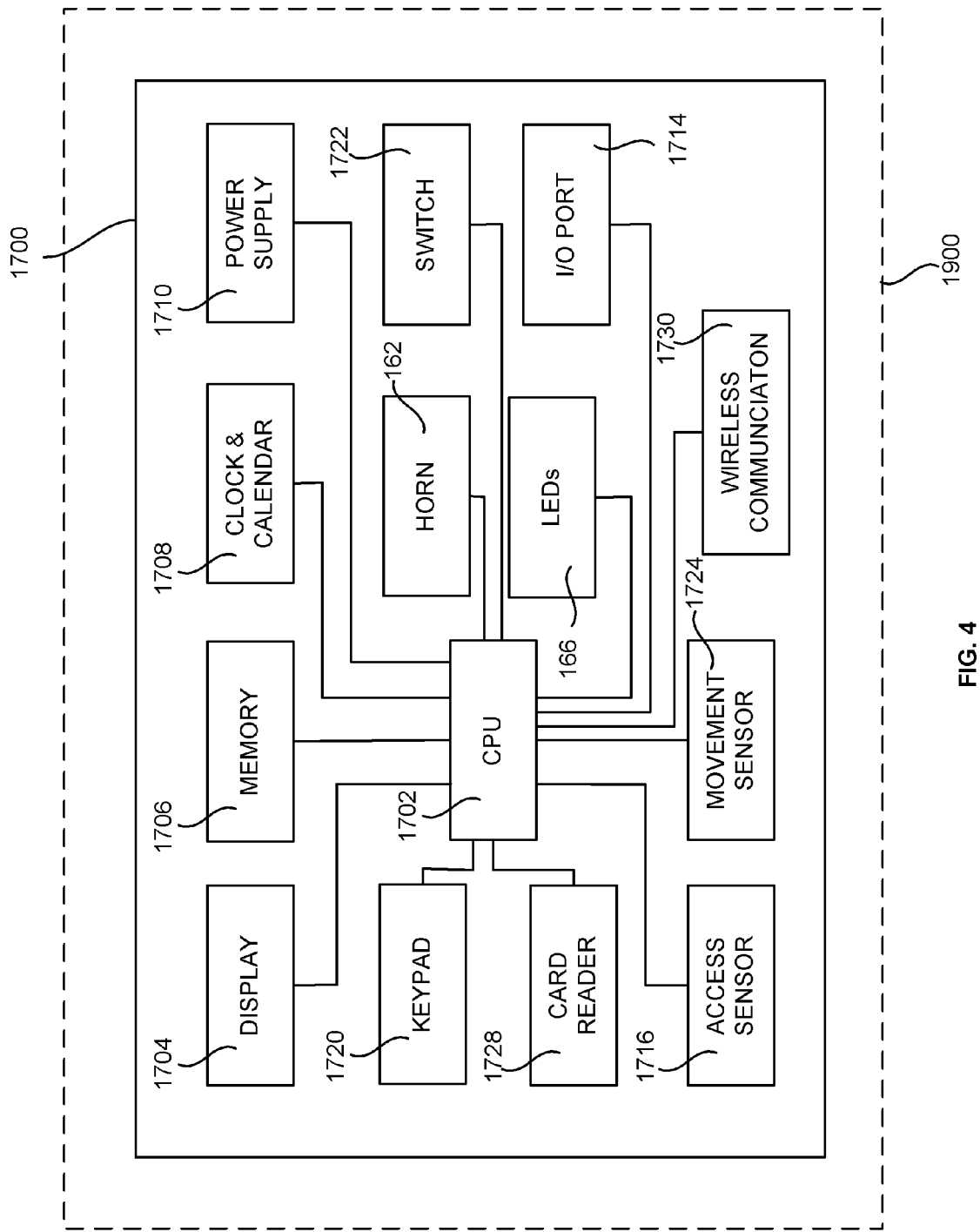
FIG. 4 is a depiction of a cart alarm control system.

The alarm system is operated by an electronic control system. In FIG. 4, the cart or other enclosed structure 1900 includes the electronic control system 1700 for controlling the security system. The alarm system may include a central processing unit (CPU) 1702, a display 1704, a memory 1706, a clock and calendar 1708, a power supply 1710, an input and output port (I/O port) 1714, an access sensor 1716, a battery warning light 1718, a keypad 1720, and a kill switch 1722. While only one sensor and kill switch are shown in the block outline, a plurality of sensors and kill switches may be used to carry out the present invention.

In another embodiment, the control system may also include a movement sensor 1724 for initiating an alarm condition based on cart movement. The movement sensor may be based on wheel movement detection, cart speed or acceleration detection, or cart distance displacement. The movement sensor 1724 may be an accelerometer, a strain gauge, GPS (global positioning system) tracking unit, RFID system, or another type of sensor used to detect movement.

The control system may detect movement of the cart over a predetermined period of time. In some situations, the cart may need to be moved not related to use of the cart. For example, the cart may need to be moved to access areas behind a cart. It is desirable to not have such movement trigger an alarm condition, as this movement does not indicate use of the cart. By detecting movement with respect to time (e.g., movement over a period greater than a predetermined time period), it is possible for the controller to detect if the movement is just a few feet or a larger distance. As such, the controller may be able to differentiate between a time when the cart is being repositioned in a storage location and a time when the cart is being moved to a different location for use of the cart's contents. As such, the controller need not signal an alarm condition to indicate access or a need to restock the cart when the cart has merely been moved a few feet or bumped. On the other hand, when the movement sensor detects motion for more than a predetermined period of time, the alarm condition may be initiated. In other embodiments, mechanisms other than time may be used to gauge the amount of movement. For instance, a GPS system (or other sensor) may detect actual distance traveled, absent a time measurement. Alternatively, the movement sensor may be a location based sensor, such as an RFID sensor, which determine that the sensor attached to the cart is no longer within range of a sensor reader located near the storage location. Preferably, the present invention will have mechanisms for detecting whether movement is more than incidental. Such mechanisms are known in the art and will not be discussed herein.

Memory 1706 comprises non-volatile memory, RAM, ROM, or another storage device. The clock may be used to terminate the audible alarm after a predetermined period of time in order to save power, and the calendar information may be used to determine content storage time so that the contents of the cart are kept up to date. The data and time may also be used for tracking purposes. For example, date and time may be used in conjunction with a GPS or RFID system to track the location of the cart. Display 1704 may comprise an alphanumeric LCD display or the like as shown in FIG. 5, and may display information related to the alarm state or other information regarding the cart's contents. Alternatively, an LED or multiple LEDs 166 may be provided to indicate a low battery warning or that the cart is secure or that the cart has been accessed. An LED or other visual indicator may be placed in a steady on state or a blinking on state.

One LED element may be equipped with multiple light emitting diodes of different colors to indicate the different states of the cart. When used in mobile carts, the present invention will preferably be battery operated. While, battery life is not expected to be a major factor, due to infrequency of access, it is nonetheless beneficial to providing a multiple-color LED on the outside of the cart. For example, green will indicate that the cart is secure and yellow may indicate that the battery level is low. The same LED element, or a separate LED, may emit yellow light when the cart has a low battery. It is also possible, however, to provide for an additional color in order to have another indication that the cart's contents have been previously accessed. Another larger display may be provided in order to allow text based display messages to be presented by the cart.

The power supply 1710 may comprise a standard alkaline battery or a rechargeable nickel-cadmium (NiCd) battery, featuring unattended fast charging with automatic kick-down to standby charging. Power supply 1710 also allows for connection for wall powered use independent from battery presence or charge level. The battery warning light on the display 1704 is illuminated by CPU 1702 if the battery power is below a predetermined level. The power supply comprises circuitry (not shown) to survive accidental connection to other than a supplied wall transformer, e.g., A.C. or D.C. of less than 30 volts. Furthermore, the power supply 1710 may also include a backup battery cell, which may be a lithium battery cell, preferably with a life expectancy of over five years. The battery warning light may be flashed or powered in a steady state. By flashing the warning light, battery power may be conserved by cycling the control system between a low power state and a standard operating state.

I/O port 1714 comprises a standard port for interconnection with a personal computer. The I/O port may be a network communication port for connecting the cart to another computing device, or may be port for coupling an I/O device such as a keyboard or a printer. The wireless communication unit 1730 may include a transceiver for coupling to another computing device to send and receive messages. Sensor 1716 may comprise, for example, a magnetic sensor that detects if the securing bar is in a latched position. Keypad 1720, as shown in FIG. 5, preferably comprises a membrane touchpad with ENTER key, CLEAR key, 0 through 9 keys, and other operation keys including a LOCK key, PIN key, TIME key, AUDIT key, and ADD/DEL key. Other keys may include a SILENCE key and a RESET key.

The SILENCE key may be used to implement a silence function to silence the alarm when the sensor determines that the cart has been accessed. When a pin has been entered, the cart can be placed in a silent mode that displays a visual indication that the cart has been accessed, but does not sound the horn indicating that access has occurred. As such, it is possible to prevent an audible alarm from sounding, while still providing notice to users that the cart has been accessed.

Audit keys can be used by the pharmacy when restocking the cart after an alarm event. When individual sensors are used for each of the plurality of storage sections, it is possible to keep an individual log of the sections that have been accessed. The audit function will display a readout that states which storage sections of the cart have been accessed to allow a pharmacy to restock only the sections of the cart that have been accessed. Alternatively, the I/O port or wireless communication unit may be used to determine which sensors caused the alarm state to be triggered. As such, the pharmacy will not have to spend time taking an inventory of the sections of the cart that have not been accessed. The pharmacy may also enter information to be stored in the memory regarding the quantity or expiration dates of items stored in the cart, so that the time spend inventorying the cart can be minimized and personnel may be made aware of the need to replace medications in the cart which are expiring. Alternatively, the expiration dates of drugs may be stored in the cart's memory and the cart can be controlled to transmit a wireless communication when an expiration date is approaching or has arrived. As such, it is beneficial for the alarm controller to recognize a reset condition from the secure state. The RESET key can be used to reset the system when the cart has been fully stocked after the cart has been accessed. Alternatively, a predetermined key code may be used, with or without a RESET key, to reset the cart to a secure access state.

FIG. 6 shows a cart, with wheels and drawers, in which the present invention may be employed. The cart includes tilt-out bins 108 and drawers 112. Additional equipment may be attached to the cart, as shown. For example, defibrillator 604 may be provided on the cart for resuscitation and a tank 608 for supplying oxygen, or other gases, may also be attached to the cart. The body of the cart hides the sensors and kill switches from view of the cart operator. The controller for controlling the cart security system may be disposed as an attachment in the same manner as the defibrillator or may be disposed internally in the cart in the same manner as a sensor. As such, a user of the cart may notice little visual difference between carts of the present invention and prior art carts.

Figure 7:
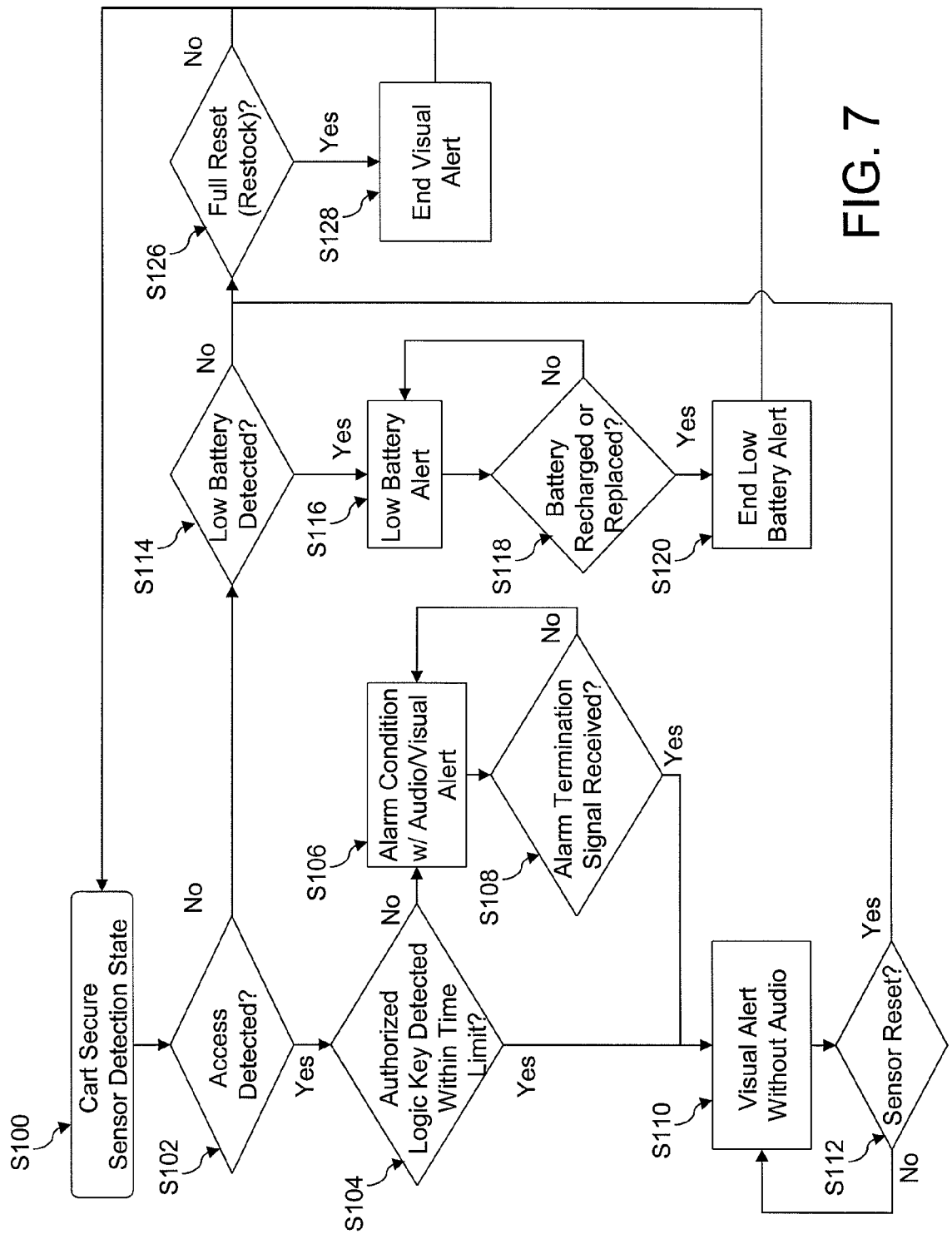
FIG. 7 is a flow chart describing example computer logic of the present invention.

FIG. 7 depicts a flow chart describing an example of computer logic for securing a cart of the present invention. A crash cart of the present invention is preferably stocked with supplies and placed to be readily accessible in the event of a medical emergency. When the cart is stored in such a location, an alarm controller may be set to receive inputs from a number of detectors. In particular, the alarm controller will receive signals from one or more of a battery detector, an access detector, a motion detector, and another input device. When the alarm controller receives a signal, it determines which of the signals it has received. While FIG. 7 depicts an example control logic that controls each input, the functions of the alarm controller could be implemented separately.

When the alarm controller receives a signal from an input device, the alarm controller first determines if the signal is an access detection signal from a sensor indicating that a compartment section has been accessed (S102). When the alarm controller determines that an access signal has been detected (S102), the alarm controller may then determine if an authorized logic key was detected within a predetermined time limit (S104). If no authorized logic key was detected, the alarm controller proceeds to initiate an alarm condition with both audio and visual alerts (S106). (If no input device is provided for entering an authorized logic key, the alarm controller will initiate the alarm condition (S106) as soon as access is detected.) The access signal may be transmitted from an access sensor. For example, when a securing bar is provided on the cart, a sensor on the movable securing bar will detect movement of the securing bar (S102) and will transmit a signal to the alarm controller, so that the alarm controller will initiate the alarm condition (S106). The alarm condition may include an audio and visual alert. The audio alert portion of the alarm will continue until an alarm termination signal is detected (S108). The alarm termination signal may be sent from a kill switch, a keypad, or from another input device. However, when the alarm termination signal is received by the alarm controller, the cart continues to provide a visual alert (S110), in order to indicate that the cart may not be fully stocked.

If, in S104, it is determined that a proper logic key has been entered within the time limit, the visual alert is provided without the audio alert (S110). For instance, if an authorized logic key was entered less than 30 seconds or 1 minute prior to detection of access, the condition could be met. A user may input a logical key code into a keypad, or into another input device used to enter identification and/or authorization information. After the authorized logic key has been entered, the alarm controller remains in the secure state and continues to monitor for access events. When an access event has been detected in S102, the alarm controller determines whether the logic key is authorized and whether the logical key was detected within a predetermined period of time (S104), relative to the access event. If the time limit elapses, the cart returns to a normal state. As such, when personnel enter a logical key, but do not actually access the contents of the cart, the cart is able to retain a secure state.

As discussed, in S110 a visual (e.g. restocking) alert is provided, but not the audio (e.g. security) alert. The visual alert may include multiple visual indicators. The visual alert in S110 may be the same as the visual alert initiated at the time the alarm condition is initiated, which is continuously provided after the audio alert is terminated, or may be a different or additional visual alert which is initiated after the alarm termination signal is received (or in connection with the use of a logical key). For example, after an alarm termination signal, a blinking alarm condition LED may be turned off, though a cart access LED may be changed from a secure color (e.g. green) to a color indicating that the cart has been accessed (e.g. red).

In addition, after an authorized logical key is entered, but prior to access, the indicator may provide a visual alert that notifies personnel that the cart is in an intermediate state. For example, a multi-color LED may be provided for indicating an alarm condition. This LED may be green when the cart is secure, yellow in the intermediate state, and red when the cart is in the alarm condition. This indicator can inform a cart user whether the predetermined time for accessing the cart, after the logical key has been entered, has expired. The indicator may also be used to indicate to the user whether the logical key entered is an authorized logical key. As such, a user may be provided an indication of whether or not the audio alarm will sound when the cart is accessed.

With the audio alert terminated in S108 (although the visual alert may indicate a need for restocking in S110), the sensor may be reset (S112) to return the program to detection state (S100). For example, when a movable securing bar is returned to a secured position, the sensor will recognize that the bar has been reset to the secure position, indicating that the cart is no longer being accessed, and may return to its detection state. In a preferred embodiment, after the sensor reset is detected in S112, the alarm controller determines whether a full restock has been detected (S126). Of course, the sensor reset or full reset may be detected without the alarm termination signal being sensed.

The cart also monitors for a low battery state (S114). If a low battery is detected, the controller initiates a low battery alert (S116) by a low battery indicator, such as an LED. After the low battery indicator is initiated, the battery is monitored to determine if the battery is recharged or replaced (S118). After the battery is recharged or replaced, the low battery state is ended (S120). As discussed above, when the battery is low, the alarm controller may set the low battery indicator to be continuously on, or may use a blinking light along with power cycling to lower the amount of power used for this function. While in the low power state, the alarm controller will continue to receive sensor signals that indicate access or input device signals indicating the entry of a logical key. That is, as shown in FIG. 7, the controller continues to monitor the battery in S118 to determine if the battery is recharged or replaced, but also monitors the sensors and input devices for other input events, such as access events or the entry of an authorized logical key. Thus, a low battery state will not impede detection of access to the cart.

Ordinarily, a crash cart will be taken to a pharmacy to be restocked after use. After the cart has been inventoried and restocked, the cart is ready to be used again and needs to be reset to a secure state. As such, a logical key or other mechanism may be used to fully reset the cart (S126). This logical key may be a different logical key which is unique to pharmacy personnel or may be a specific logical key which indicates a restock or other full reset event to the alarm controller. This may be entered by personnel through a keypad or other input device, or may be entered through the I/O port or by wireless communication. When the controller detects a full reset (S126), the visual alert of an alarm condition and/or that the cart has been previously accessed is ended (S128), and the cart is returned to the secure sensor detection state (S100). If a full reset has not been detected, however, the cart will return to the secure sensor detection state (S100), but the visual alert will not be terminated. That is, the cart will continue to provide an indication to potential users that the cart may not contain a full compliment of supplies, yet still be secure.

A full reset (S126) may be a multi-part process, which requires that a logical key be entered along with other information regarding the supplies that are stored in the cart, before the cart is secured. For instance, when the cart is being restocked, the cart may accept information regarding the supplies to be stored in the cart, including the type of supplies or information about the supplies, such as quantities or expiration dates. This information may be entered through an input device on the cart or through the input port or wireless communication unit. Reminders may be transmitted from the cart (or other computer) to the appropriate personnel indicating that certain supplies need to be replaced. This may be in the form of an additional alarm condition or alert. A full reset may also be determined based upon the connection status of the cart. For example, a full reset process may be determined to begin when a device begins communicating with the cart through the input port or wireless communication unit, and may end when the external device is no longer in communication with the cart.

While the present invention has been described with respect to what is presently considered to be the preferred embodiments, the present invention is not limited to the disclosed embodiments. Rather, the present invention covers various modifications and equivalent arrangements included within the spirit and scope of the appended claims. The scope of the appended claims is to be accorded the broadest interpretation so as to encompass all such modifications and equivalent structures and functions.

What is claimed is:

1. A cart comprising:
   a housing having a top surface portion and a plurality of sides;
   a compartment section, for storing items in said housing, which is associated with and accessible from at least one side of said housing, wherein said compartment section may be placed in (a) a closed condition for preventing removal of items stored therein, and (b) an open condition for permitting access to items stored therein;
   a sensor for sensing movement of said compartment section from the closed condition to the open condition;
   an alarm indicator for signaling an alarm condition;
   an alarm controller, coupled to said sensor and said alarm indicator, wherein said alarm controller controls said alarm indicator to signal the alarm condition when said sensor senses movement from the closed condition to the open condition; and
   a termination mechanism, coupled to said alarm controller, for transmitting an alarm termination signal when said termination mechanism is triggered by a user, wherein said termination mechanism is located in said compartment section.

2. The cart of claim 1, wherein said termination mechanism is not accessible when said compartment section is in the closed condition.

3. A cart comprising:
   a housing having a top surface portion and a plurality of sides;
   a compartment section, for storing items in said housing, which is associated with and accessible from at least one side of said housing, wherein said compartment section may be placed in (a) a closed condition for preventing removal of items stored therein, and (b) an open condition for permitting access to items stored therein;
   a sensor for sensing movement of said compartment section from the closed condition to the open condition;
   an alarm indicator for signaling an alarm condition;
   an alarm controller, coupled to said sensor and said alarm indicator, wherein said alarm controller controls said alarm indicator to signal the alarm condition when said sensor senses movement from the closed condition to the open condition; and
   a termination mechanism, coupled to said alarm controller, for transmitting an alarm termination signal when said termination mechanism is triggered by a user, wherein said termination mechanism is hidden on a side surface of the cart.

4. The cart of claim 1, wherein said alarm indicator comprises an audible alarm indicator for providing an audible signal of the alarm condition.

5. The cart of claim 4, further comprising:
   an input device coupled to said alarm controller,
   wherein said alarm controller prevents said audible alarm indicator from signaling the alarm condition when a logical key is entered before said sensor determines movement from the closed condition to the open condition, and said alarm controller terminates the signaling of the alarm condition by said audible alarm indicator when a logical key is entered after said sensor determines movement from the closed condition to the open condition.

6. The cart of claim 1, further comprising a movable bar for securing said compartment section in the closed condition by engaging a compartment section retaining portion when said movable bar is in a securing position.

7. The cart of claim 6, wherein said alarm controller is returned to a status detecting state when said movable bar is returned to the securing position.

8. The cart of claim 1, wherein said compartment section comprises a plurality of compartments, each of said compartments being capable of storing items and being placed in the closed position and the open position.

9. The cart of claim 1, wherein said alarm indicator comprises a remote digital communication unit, coupled to said alarm controller, that digitally transmits an alarm condition to a remote receiving device.

10. The cart of claim 1, wherein said alarm indicator comprises a visual indicator located on said housing of the cart, and wherein said visual indicator visually indicates the alarm condition when said sensor detects movement from the closed condition to the open condition and visually indicates that the cart has been previously accessed after the alarm condition has been terminated.

11. The cart of claim 10, further comprising:
a battery; and
a battery condition sensor,
wherein said visual indicator indicates that said battery is low on power when said battery condition sensor determines that the power level of said battery is below a predetermined battery power level.

12. The cart of claim 1, further comprising a movement sensor which senses movement of the cart from a first location to a second location.

13. A cart comprising:
a housing having a top surface portion and a plurality of sides;
a plurality of compartments, for storing items in the cart, which are associated with and accessible from at least one side of said housing, each of said compartments being selectably accessible by being placed between (a) a closed condition for preventing removal of items stored therein, and (b) an open condition for permitting access to items stored therein;
a plurality of sensors, wherein each of said plurality of sensors is respectively associated with a different one of said plurality of compartments and senses when said respective compartment is moved from the closed condition to the open condition;
an alarm indicator for signaling an alarm condition;
an alarm controller, coupled to said sensors and said alarm indicator, wherein said alarm controller controls said alarm indicator to signal the alarm condition when one of said sensors senses movement of said respective compartment from the closed condition to the open condition; and
a termination mechanism, coupled to said alarm controller, for transmitting an alarm termination signal when said termination mechanism is triggered by a user, wherein said termination mechanism is either hidden or not accessible when each of said plurality of compartments is in the closed condition.

14. The cart of claim 13, wherein said alarm indicator comprises an audible alarm indicator.

15. The cart of claim 13, wherein said termination mechanism is hidden on a side surface of the cart.

16. The cart of claim 13, said cart further comprising an input device coupled to said alarm controller,
wherein said alarm controller prevents said audible alarm indicator from signaling the alarm condition when a logical key is entered before said sensor determines movement of from the closed condition to the open condition, and said alarm controller terminates the signaling of the alarm condition by said audible alarm indicator when a logical key is entered after said sensor determines movement from the closed condition to the open condition.

17. The cart of claim 13, wherein said termination mechanism comprises a switch located in at least one of said plurality of compartments, wherein said switch is not accessible when said at least one compartment is in the closed condition.

18. The cart of claim 13, wherein said alarm indicator further comprises a wireless communication unit, coupled to said alarm controller, that transmits the alarm condition to a remote receiving device.

19. The cart of claim 13, wherein said alarm indicator comprises a visual indicator located on said housing of the cart,
wherein said visual indicator visually indicates the alarm condition when one of said sensors detects movement from the closed condition to the open condition and visually indicates that the cart has been previously accessed after the alarm condition has been terminated.

20. The cart of claim 13, further comprising:
a battery; and
a battery condition sensor,
wherein said visual indicator indicates that said battery is low on power when said battery condition sensor determines that the power level of said battery is below a predetermined battery power level.

21. The cart of claim 13, further comprising a securing bar for securing said plurality compartment sections in the closed condition by engaging a plurality of compartment section retaining portions when said securing bar is in a securing position,
wherein said securing bar may simultaneously disengage said plurality of compartment section retaining portions when said securing bar is moved from the securing position to an unsecured position to place said plurality compartment sections in the open condition.

22. A method of securing medical supplies in a cart, the method comprising the steps of:
providing a cart comprising (1) a housing having a top surface portion and a plurality of sides, (2) a compartment section for storing items in the housing and which may be placed in (a) a closed condition for preventing removal of items stored in the compartment section, and (b) an open condition for permitting access to items stored in the compartment section, (3) a sensor for sensing movement from the closed condition to the open condition, (4) an alarm indicator for signaling an alarm condition, (5) an alarm controller, coupled to the sensor and the alarm indicator, and (6) a termination mechanism, coupled to the alarm controller, for transmitting an alarm termination signal when the termination mechanism is triggered by a user, wherein the termination mechanism is either hidden or not accessible when the compartment section is in the closed condition;
arming the alarm controller after medical supplies have been stocked in the storage compartment of the cart and the cart has been placed in the closed condition; and
causing the alarm indicator to signal an alarm condition when the alarm controller determines that the sensor has sensed movement from the closed condition to the open condition.

23. The method of claim 22, wherein said causing step causes the alarm indicator to wirelessly transmit the alarm condition to a remote location in a hospital.

* * * * *